United States Patent [19]

Grambush et al.

[11] Patent Number: 5,111,029
[45] Date of Patent: May 5, 1992

[54] COMPACT HEAT DISINFECTION UNIT FOR CONTACT LENSES

[75] Inventors: Douglas H. Grambush, Laguna Beach; Gregory R. Holland, Irvine; Walter A. York, El Toro, all of Calif.

[73] Assignee: Allergan, Irvine, Calif.

[21] Appl. No.: 587,662

[22] Filed: Sep. 24, 1990

[51] Int. Cl.⁵ ............................. A61L 2/00; H05B 3/06
[52] U.S. Cl. ..................................... 219/521; 219/386
[58] Field of Search ...................... 219/385, 386, 521

[56] References Cited

U.S. PATENT DOCUMENTS

| | | | |
|---|---|---|---|
| D. 289,923 | 5/1987 | Hoogesteger | D24/9 |
| 3,983,362 | 9/1976 | Hoogesteger | 219/521 |
| 4,242,572 | 12/1980 | Thomas | 219/521 |
| 4,472,623 | 9/1984 | Futter | 219/521 |
| 4,481,410 | 11/1984 | Bortnick | 219/521 |
| 4,578,566 | 3/1986 | Bowen | 219/521 |
| 4,677,280 | 6/1987 | Kai | 219/385 |
| 4,701,597 | 10/1987 | Braun | 219/521 |
| 4,873,424 | 10/1989 | Ryder | 219/521 |

Primary Examiner—Teresa J. Walberg

[57] ABSTRACT

A compact heat disinfection unit for contact lenses including a waterproof unit having a chamber receiving therein a closed lens case. A heater is disposed in the unit for heating the case. The unit has a retractable blade assembly which folds back into the unit and is electrically coupled to the heater for actuating the same. A push button, accessible from the exterior of the unit, is provided for actuating the heater. The covers of the lens case cannot be removed while heating the same.

22 Claims, 4 Drawing Sheets

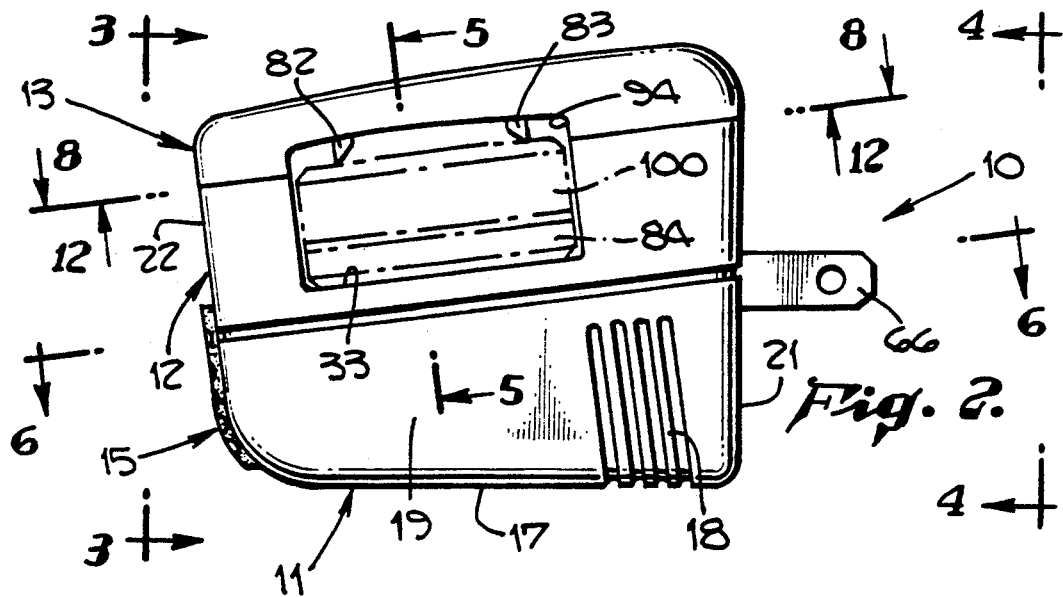
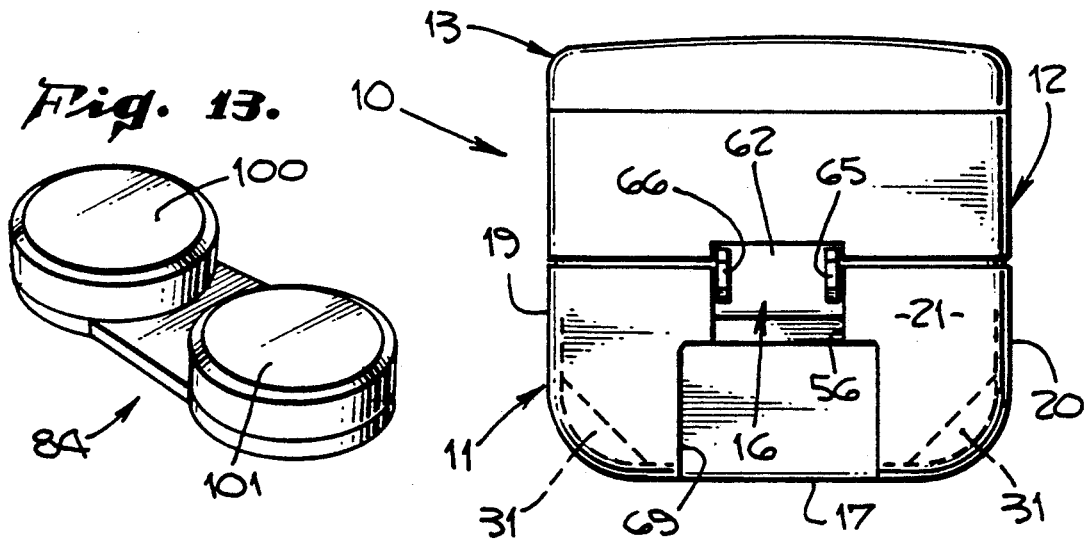
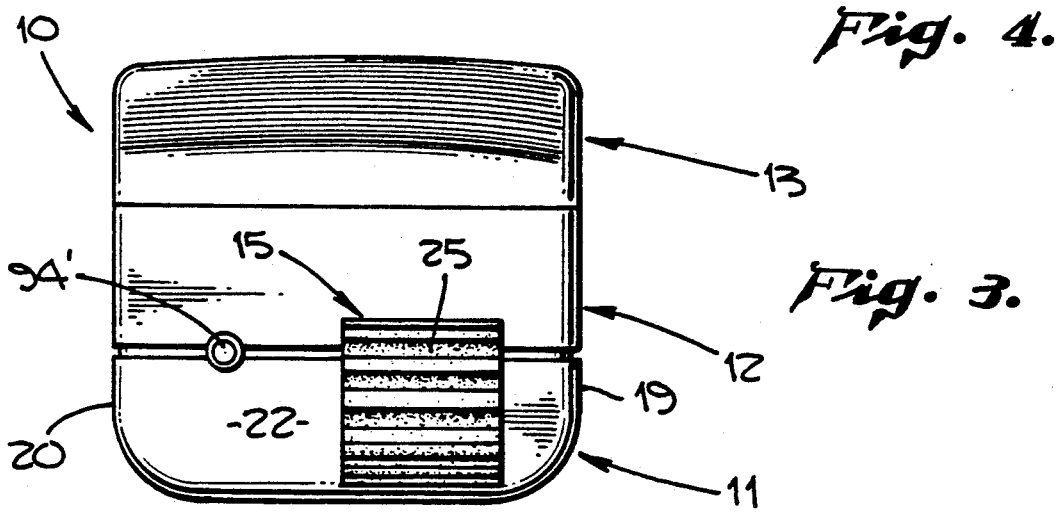

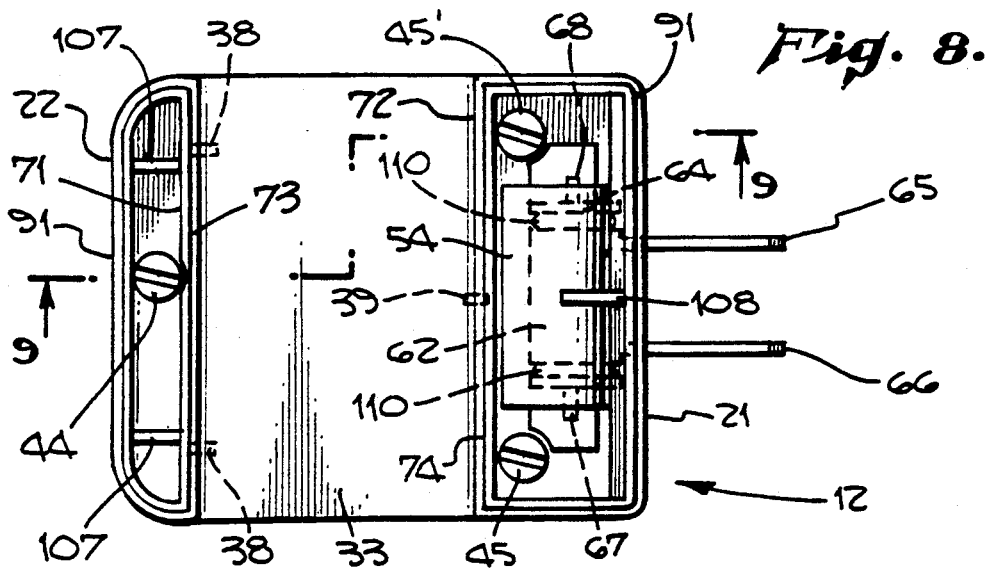
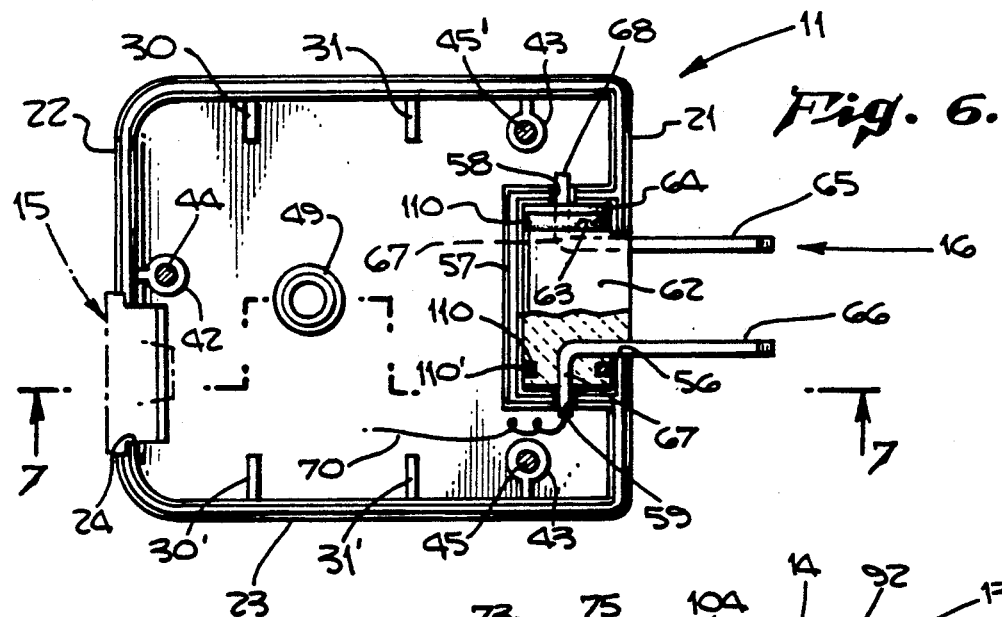
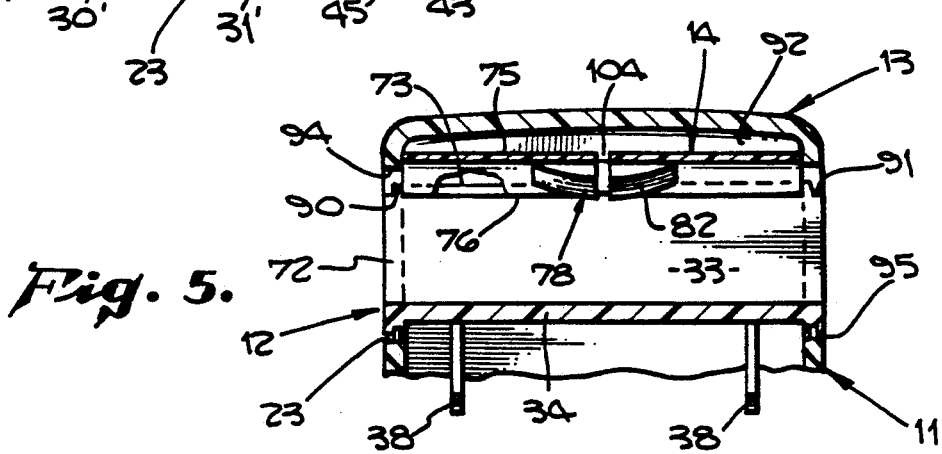

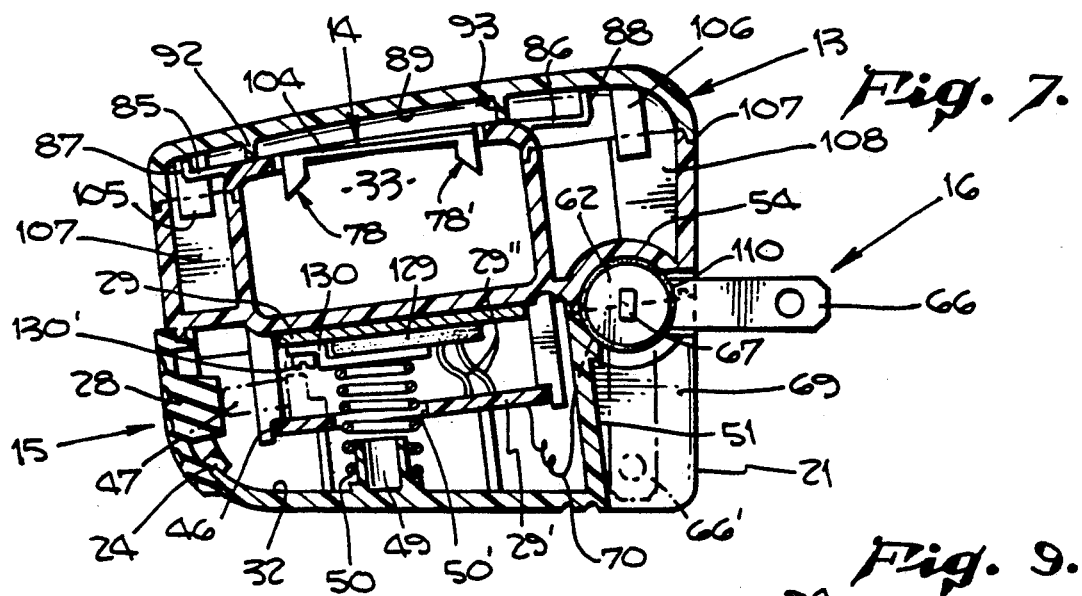
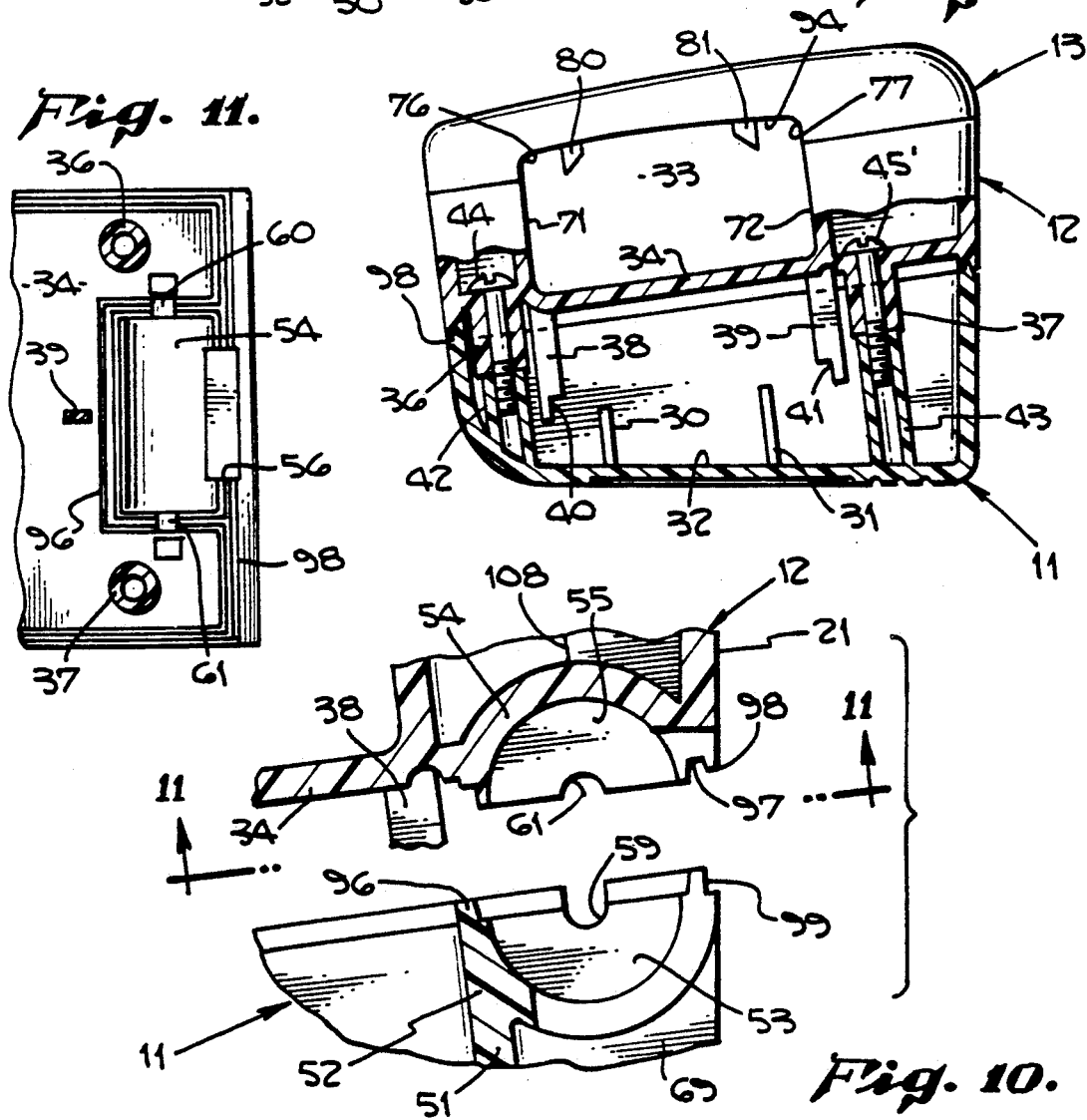

COMPACT HEAT DISINFECTION UNIT FOR CONTACT LENSES

BACKGROUND OF THE INVENTION

1. Field of the Invention

The present invention generally relates to a compact heat disinfection unit for contact lenses and, more specifically, to a compact heat disinfection unit for contact lenses with additional safety features which utilizes low heat levels, a retractable blade assembly, and a separate dual compartment lens case to contain the solution and lenses.

2. Description of the Prior Art

In the past, the need to periodically clean and store contact lenses has been well known. This need was met by a variety of contact lens disinfection units. For example, Bowen, U.S. Pat. No. 4,578,566, discloses a contact lens disinfecting unit comprising a plastic housing, compartments for the lenses within the plastic housing, an electrically energized heating means, and electrical circuitry to connect the heating means to the energizing source. Subsequently, however, a need was felt for contact lens disinfection units which are suitable for portable use. Attempts to meet this need resulted in Braun, U.S. Pat. No. 4,701,597. Braun discloses a contact lens disinfection which comprises chambers for the lenses, a heating element, heat sinks coupled to the heating elements and the chambers, a thermostat, a thermostat heat sink, and a heat transfer element for transferring a controlled amount of heat from the heating element to the thermostat heat sink.

Despite the compact size of the lens disinfection units, problems with their use still existed. For example, the design of the units such as in Braun encouraged users to place the lens case on top of the unit and pour saline solution directly into the lens compartment while the unit was plugged into an electrical outlet. This created problems of saline solution spilling over from the lens case onto the unit and causing short-circuiting within the unit. In U.S. Pat. No. 4,873,424, another attempt to solve these prior art problems was disclosed. However, the Ryder device would allow a user to place a lens case on top of the unit to pour solution therein, allowing the same to possibly enter inside the unit. Also, there are no foldable contacts or hinged blades in Ryder allowing compact storing and travel. The Ryder unit requires one to plug it into the wall (which turns it on), then grasp the unit with wet hands (conventional cleaning of contacts involves washing of the lens in one's hands which results in wet hands) which might result in water and/or saline solution short-circuiting the device of the wall outlet. Further, in Ryder, there is nothing holding or bracing the case B inside the unit and centering the same therein for uniform heating.

Prior compact lens disinfection units that are suitable for traveling purposes generally have protruding parts, such as the blade assembly which can catch on clothing or the like. That is, prior art units are comprised of several loose parts, and require a non-folding electrical plug which tends to catch on other items in the user's luggage. Therefore, a need exists for a compact disinfection unit with additional safety features which are suitable for convenient traveling purposes.

SUMMARY OF THE INVENTION

It is an object of this invention to provide an improved compact heat disinfection unit for contact lenses.

It is another object of this invention to provide a compact heat disinfection unit in which the lens case is confined within a compartment within the unit.

It is yet another object of this invention to provide a compact heat disinfection unit having a retractable blade assembly for convenient travel.

It is a further object of this invention to provide a compact heat disinfection unit which deters one from pouring saline solution into the lens case while the unit is in use.

It is still another object of this invention to provide a compact heat disinfection unit which can be actuated by pushing a button as a user will not have to grasp the unit with wet hands.

The foregoing objects of this invention are preferably accomplished by providing a compact heat disinfection unit for contact lenses comprising a waterproof unit having a chamber receiving therein a closed lens case. A heater is disposed in the unit for heating the compartment. The unit has a retractable blade assembly which folds back into the unit and is electrically coupled to the heater for actuating the same. A push button, accessible from the exterior of the unit, is provided for actuating the heater. The caps of the lens case cannot be removed while heating the same.

BRIEF DESCRIPTION OF THE DRAWING

FIG. 2 is an assembled view of the unit of FIG. 1;

FIG. 3 is a view taken along lines 3—3 of FIG. 2;

FIG. 4 is a view taken along lines 4—4 of FIG. 2;

FIG. 5 is a cross-sectional view of a portion of the unit of FIG. 1 taken along lines 5—5 of FIG. 2;

FIG. 6 is a view taken along lines 6—6 of FIG. 2;

FIG. 7 is a view taken along lines 7—7 of FIG. 6;

FIG. 8 is a view taken along lines 8—8 of FIG. 2;

FIG. 9 is a view taken along lines 9—9 of FIG. 8;

FIG. 10 is a detailed sectional view of a portion of the unit of FIG. 7; and

FIG. 11 is a view taken along lines 11—11 of FIG. 10;

FIG. 13 is a perspective view of a lens compartment used in accordance with the teachings of the invention.

DETAILED DESCRIPTION OF THE PREFERRED EMBODIMENT

Figure 1:
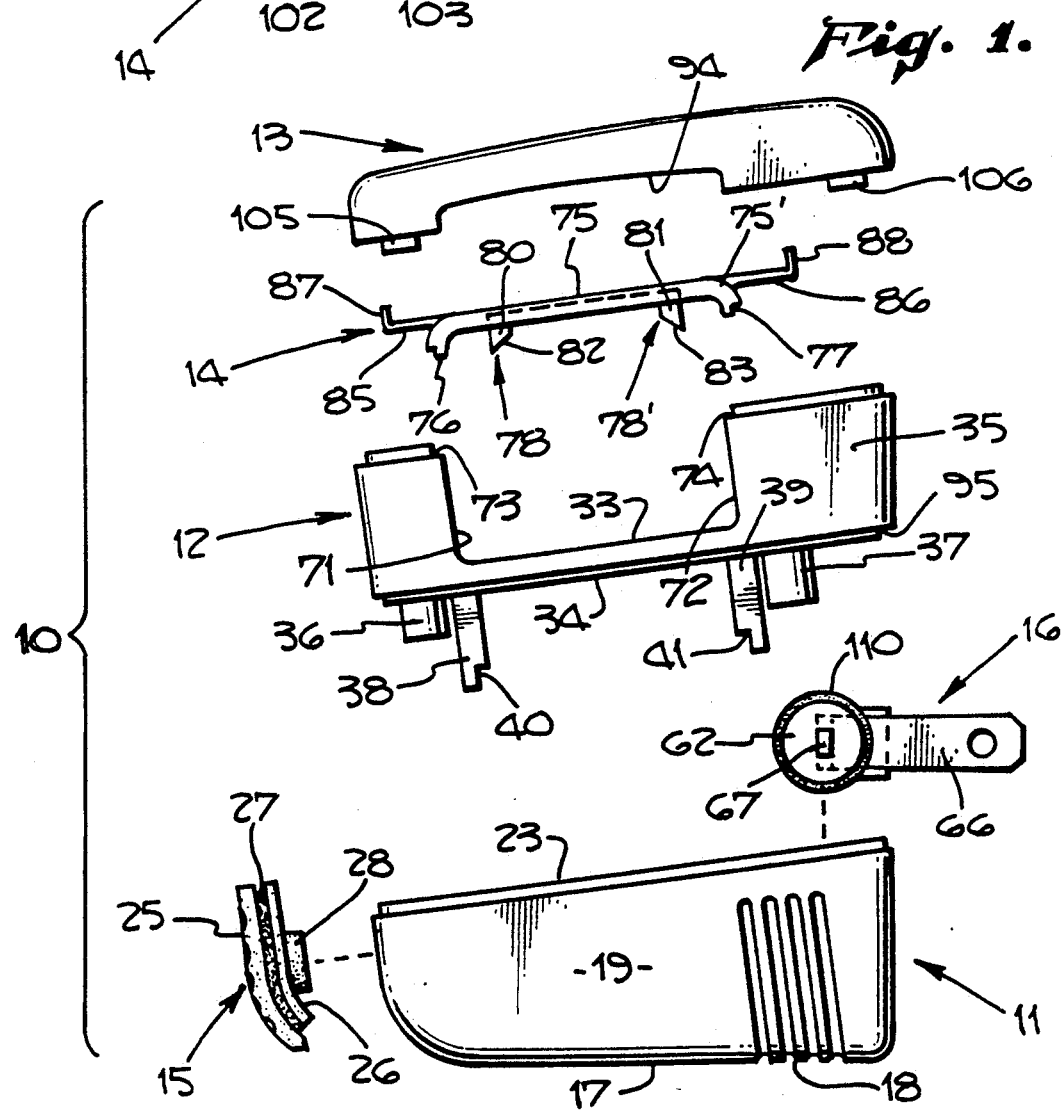
FIG. 1 is an exploded view of the compact heat disinfection unit in accordance with the teachings of the invention.

Referring now to the drawing, FIG. 1 shows a compact heat disinfection unit 10 comprised of a bottom housing member 11, a center housing member 12, a housing cap 13, a resilient clip 14, a push button assembly 15, and a retractable blade assembly 16. Unit 10 is shown in assembled view in FIG. 2.

Bottom housing member 11 (FIG. 2) has a flat bottom wall 17 and a plurality of ribs 18 to provide a grip for the surface on which unit 10 is disposed. Side walls 19, 20 (FIG. 4) are interconnected by rear wall 21 and front wall 22 (FIG. 3) forming an enclosure for unit 10. As seen in FIG. 5, the interconnected walls 19 to 22 have a peripheral stepped upper edge 23. As seen in FIG. 6, an opening 24 is provided in wall 22 receiving push button assembly 15 therein. Push button assembly 15 has a first ribbed outer wall 25 (FIG. 1) spaced from an inner wall 26 separated by a resilient interconnecting member 27. A protrusion 28 is provided on inner wall 26 extending inwardly of unit 10 when installed as in FIGS. 2 and 3. As seen in FIG. 7, walls 25, 26 straddle edge 23 (which continues around opening 24 as shown) and is thus retained in position in opening 24.

Center housing member 12 (FIG. 1) has a chamber 33 therethrough with a bottom wall 34 (FIG. 5) and an upper housing portion 35 surrounding chamber 33. A pair of spaced hollow bosses 36, 37 (FIG. 9) extend downwardly from wall 34. Boss 36 receives therein screw 44 (FIG. 8) and post 37 receives therein screw 45'. The front boss receiving screw 45 is not visible in FIG. 9. Three spaced prongs or brackets 38, 39 (FIG. 8) with stepped ends 40, 41, respectively, (FIG. 9) are disposed adjacent the bosses. As seen in FIG. 9, bosses 36, 37 are aligned with bosses 42, 43 receiving threaded screws 44, 45', respectively (screw 44 in aligned bosses 36, 42 and screw 45' in aligned bosses 37, 43). Screw 45 (FIG. 6) and its aligned bosses are not visible in FIG. 9. The screws may be self-threading, if desired.

As seen in FIG. 7, heating means is provided in the form of a heat plate 29, such as a zinc-plated steel plate, having a heat element 129, operatively coupled to a heating element and a circuit board 29' is disposed internally of housing member 11 supported by a spring 50. Circuit board 29' is mounted between spaced brackets 38, 39 having a flanged end 46 conforming to stepped ends 40, 41 of brackets 38, 39. A push button 47 extends past bracket 38 (FIG. 7) engaging protrusion 28. It can be appreciated that pushing push button assembly 15 inwardly against the resilience of member 27 pushes button 47 thereby activating heat element 129. As seen in FIG. 7, spring boss 49 is provided on interior wall 32 receiving a spring 50 thereon. Spring 50 passes through a hole 50' in circuit board 29', abuts against strap 130, and braces the strap 130, heating element 129, and heat plate 29 upwardly. A rivet 130' threads through a hole in an offset portion in strap 130, then threads into a suitable hole in plate 29 to retain strap 130 to plate 29. If desired, a rivet may be used in place of screw 130' to hold the strap 130 to plate 29.

Bottom housing member 11 also has a partition wall 51. Wall 51 terminates at the top in an enlarged curved flange portion 52 (FIG. 10) which extends to wall 21 forming an arcuate semicircular chamber 53. Wall 34 of center housing member 12 also terminates in an arcuate flange 54 forming an arcuate semicircular chamber 55 adapted to mate with chamber 53 (FIG. 7). As seen in FIG. 4, a slot 56 is provided in rear wall 21 aligned with the cylindrical chamber formed by the mating of chambers 53, 55. As seen in FIG. 6, a generally rectangular partition wall 57 extends from one side of opening 56 to the other, having spaced slots 58, 59 therein. Slots 58, 59 are preferably arcuate (see FIG. 9 where slot 59 only is visible) and adapted to conform to like configured slots 60, 61 (see FIG. 11—slot 61 is only visible in FIG. 10).

Blade assembly 16 includes a main generally cylindrical portion 62 (FIGS. 6 and 8) having a reduced end 63 (FIG. 6) interconnecting portion 62 to an integral end portion 64. Both blades 65, 66 are electrically conductive material, integral with portion 62, which is of an electrically insulative material. Each blade 65, 66 has an extension portion 67 extending thereout mounted between mating slots 59, 61. An extension portion 68 extends from end portion 64 and is mounted in mating slots 58, 60. As seen in FIGS. 4 and 7, a slot 69 is provided in front wall 21 below blades 65, 66. Thus, blade assembly 16 can be rotated from the solid line position shown in FIG. 7 to the dotted line position as indicated by blade 66'. As seen in FIGS. 6 and 7, extension portions 67 and 68 of blades 65 and 66 are separately electronically coupled to circuit board 29' by terminal 70. Terminal 70 may be a leaf spring or a stamped metal conductor, if desired.

Figure 12:
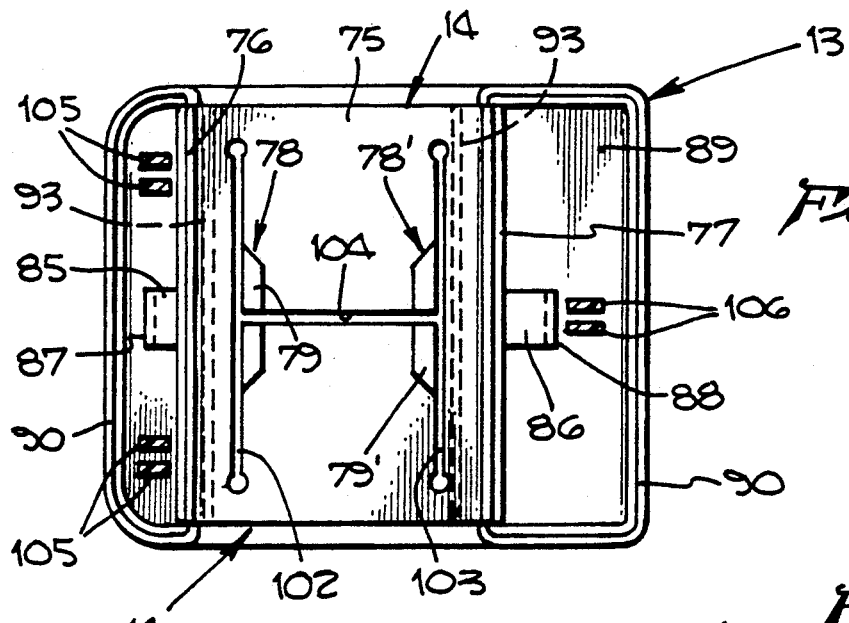
FIG. 12 is a view taken along lines 12—12 of FIG. 2.

As seen in FIG. 9, cavity 33 is defined by aforementioned bottom wall 34 of center housing member 12 and interconnected spaced side walls 71, 72. Each side wall 71, 72 terminates at the upper end in stepped edges 73, 74, respectively. As seen in FIGS. 1 and 12, clip 14 has a main generally flat body portion 75 having an arcuate lower portion 75' (see also FIG. 7) also having stepped edges 76, 77 adapted to conform to aforementioned edges 73, 74, respectively, when mounted thereon as seen in FIG. 7. Lens case guide members 78, 78' (FIG. 12) are provided in body portion 75, each having a pair of spaced generally flat main body portions 79, 79' (FIG. 12) with spaced downwardly extending alignment portions 80, 81 (FIG. 1) each having downwardly and outwardly tapered ends 82, 83, respectively, for bearing against a conventional dual compartment lens case 84 (FIG. 2), each compartment having a removable screw-threaded cover (FIG. 13) 100, 101 when inserted into cavity 33 to maintain the same in contact with bottom wall 34. A pair of resilient flanges 85, 86 (FIGS. 1 and 7) having upturned ends 87, 88 are provided on main body portion 75 of clip 14. Flanges 85, 86 may be of a resilient material adapted to bear against the underside 89 of cap 13. Cap 13 (FIG. 7) is generally rounded at its upper ends and has a lower terminal stepped peripheral edge 90 (FIG. 5) adapted to mate with upper peripheral edges 91 on the front wall 22 of rear wall 23 of center housing member 12. A pair of spaced ribs 92, 93 (FIG. 7) are provided on inner wall 89 spacing cap 13 from clip 14. Also, as seen in FIG. 1, cap 13 has a central cavity 94 adapted to conform to cavity 33 (FIGS. 2 and 7) to form a rectangular chamber for receiving lens case 84 therein. Body portion 75 (FIG. 12) may be slit, as at slits 102, 103, 104, to enhance flexibility. Also, a part of flat spaced fingers 105, 106 extend downwardly from the underside of cap 13 (FIG. 12) adapted to wedge with single walls 107, 108 on middle body portion 12 as seen in FIGS. 7 and 8.

As seen in FIG. 3, a conventional LED indicator light 94' is provided and electronically coupled to circuit board 29'. As seen in FIG. 5, wall 34 has an outer peripheral stepped edge 95 conforming to edge 23. As seen in FIGS. 7 and 10, the upper peripheral edge 96 of flange portion 52 is stepped to conform to lower peripheral edge 97 of flange 54. All of the mating stepped edges serve to prevent fluids accidentally dropped on unit 10 from flowing internally therein. The edges are such that the outer stepped portion (for example, outer portion 98 of edge 97 in FIG. 10) extends downwardly over a grooved portion 99 so that fluids may flow down portion 98 past groove 99 without entering unit 10. All the remaining stepped edges are similar. As seen in FIG. 1, the bottom housing member 11 is taller at one end than the other to provide a slope to the upper surface of cap 13 when in the assembled FIG. 2 position.

Lens case 84 is a conventional dual well lens case, each well holding a lens with solution therein. The conventional dual well lens case 84 is designed to be filled with an appropriate saline solution and so that one lens may be placed in each of the wells of the case 84. The covers 100, 101 are screw-threaded in position on the case 84 when the heat disinfection unit 10 is in use. Therefore, in order to disinfect the contact lenses, the retractable blade assembly 16 is first plugged into an electrical outlet. The dual compartment lens case 84 is then removed from the case cavity 33 (FIG. 2). The covers 100, 101 of the dual well compartment lens case 32 are removed, and the appropriate saline solution is placed in each of the wells in the case 84. One contact lens is also placed in each of the wells for disinfecting. After the lenses have been placed in the wells, the lens case covers 100, 101 are secured in position. The dual compartment lens case 84 may then be inserted into the cavity 33 of the unit 10. Once the dual compartment lens case 32 is inserted into cavity 33, a user is discouraged from removing lens case covers 100, 101 from cavity 33 while the heat disinfection unit 10 is in use. The removable dual compartment lens case 84 may further be used as a transport or storage device for the contact lenses when the user is not utilizing the heat disinfection unit 10.

As shown in FIG. 2, the cap 13 has a substantially crowned flat top surface. In previously designed disinfection units, users have been known to use the top surface of the unit as a support for resting the lens case on top thereof prior to adding a saline solution to the lens case. This situation often resulted in saline solution spilling over onto the unit causing shorting in the circuitry of the unit or shorting at the wall outlet. To prevent this situation, the housing cap 13 of the present invention is at an angle due to the shape of bottom housing member 11 so that the top surface of the housing cap 13 is at a sloped angle when the unit 10 is plugged into an electrical outlet. Therefore, when the user removes the lens case 84 from the unit 10, he cannot place the lens case 84 on the upper surface of the unit 10 to pour the saline solution into the wells. This design prevents the spilling of saline solution over onto the unit 10 while the unit 10 is in use. That is, the angle of cap 13 is steep enough to deter one from sitting or resting a lens case on top thereof. Also, the slope allows any liquids accidentally spilled on the top to roll off and away from plug 16.

The heat disinfection unit 10 thus includes a heat plate 29, the heat element 129, and circuit board 29' with electrical circuitry necessary to heat the lens case 84 to a temperature sufficient to disinfect the lenses. Switching the circuit on via push button 47 heats up the (PTC) heat element 129. This heat is transferred or conducted through the heat plate 29 and housing wall 34 to the lens case 84 in cavity 33. Thus, heat plate 29 merely warms up and transfers heat to lens case 84. Light 94' is illuminated during the heating operation. Any suitable conventional circuit board may be used which supplies current to element 129 and has a basic counter/timer circuit which shuts off the current through heating element 129 after a predetermined time interval.

The unit 10 is designed to operate at a low temperature. This feature enables the heat disinfection unit 10 to disinfect a wider range of lens material without damage to the material. The disinfection unit 10 peaks briefly at approximately 80° C., then runs at a lower temperature for the remainder of the cycle.

The heat disinfection unit 10 may be internally fused. Therefore, if a short circuit should occur in the unit 10, the user is protected from electrical shock or injury.

When the internal fuse is blown, or the circuit is damaged or interrupted for any reason, the indicator light 94' will not operate.

The configuration of the stepped edges forces water or moisture to travel uphill and through the stepped mating surfaces in order to penetrate the same and enter the unit 10 a sealant or adhesive may also be added between these joints or stepped edges. This renders unit 10 waterproof. When blade assembly 16 is not in use, it can be retracted back into slot 69 in unit 10, making unit 10 smaller and suitable for storage or traveling. O-rings 110 (FIGS. 1,6 and 10 may be provided associated with blades 65, 66 to prevent moisture from entering therepast. Thus, O-rings 110 are disposed about reduced end 62 (FIG. 6) and within groove 110'.

Any suitable materials may be used, such as heat proof plastics and the like. The unit can be of any desired dimensions but is preferably small enough for traveling and the like, but of a size sufficient to receive a dual compartment lens case therein.

We claim:
1. A compact heat disinfection unit for sterilizing contact lenses comprising:
    a housing having an internal chamber adapted to receive a covered dual compartment lens case therein;
    heating means disposed in said unit adjacent to said cavity for heating the same;
    a retractable electric blade assembly coupled to said heating means for providing electricity to the same when said blade assembly is plugged into an electric socket, said blade assembly being swivably retractable from a first storage position contained within a slot in said housing to a second operative position extending in a direction away from said housing, moisture sealing means being provided between said blade assembly and said heating means for preventing moisture from the exterior of said unit from contacting said heating means past said blade assembly;
    a button accessible from the exterior of the unit and selectively movable from an operative to an inoperative position for actuating said heating means.
2. In the unit of claim 1 wherein the upper surface of said housing is sloped from the horizontal.
3. In the unit of claim 1 wherein said heating means includes a heat plate retained within said housing under said chamber and biased toward said chamber.
4. In the unit of claim 1 wherein said housing includes a spring biased clip mounted therein above said chamber, said clip having guide means thereon extending into said chamber and into a position adapted to abut against a lens case when the same is mounted in said chamber and center said case therein.
5. In the unit of claim 1 wherein said housing includes a first bottom housing member, said button and said heating means being mounted therein, a second center housing member providing a bottom wall of said chamber and a portion of upstanding side walls forming said chamber mounted on top of said housing, said first and second housing members having said blade assembly mounted therein, and a cap closing off the upper end of said second housing member.
6. In the unit of claim 5 wherein the abutting edges of said first and second housing members and said cap are stepped with an outer downwardly extending portion mating with a slot in the mating portion to provide a leakproof unit.

7. In the unit of claim 5 including a resilient clip mounted in said housing between said cap and said second housing member, said clip mating with the side walls forming said chamber, thereby providing a cover for said chamber, said clip being biased in a direction toward the interior of said chamber.

8. In the unit of claim 1 wherein said heating means includes a circuit board having a contact thereon, a heat plate and a heat element engaging said plate mounted in said housing, said button being a resiliently mounted push button adapted to bear against said contact to actuate said circuit board to activate said element to heat said plate.

9. In the unit of claim 1 including a dual compartment lens case having a pair of removable covers closing off each of said compartments removably mounted in said chamber.

10. In the unit of claim 1 wherein said moisture sealing means includes a main generally cylindrical body portion having a pair of spaced blades extending therefrom, said body portion being journalled for swivel rotation in said slot, and a pair of resilient O-rings mounted between said body portion and its point of rotatable connection in said slot.

11. In the unit of claim 1 wherein said blade assembly has a pair of spaced elongated blades adapted to extend into an electrical socket, said button being movable in a direction generally parallel to the longitudinal axis of said blades when actuating said heating means.

12. In the unit of claim 1 wherein a tongue and groove connection is provided between said button and said housing, said button having an outer rigid portion, an intermediate resilient portion and an inner rigid portion engaging said heating means, said resilient portion allowing said outer rigid portion to move toward said inner rigid portion when pushed.

13. A compact contact lens heat disinfection unit comprising:
 a housing having a bottom housing member, a center housing member attached in a leak-resistant manner to said bottom housing member, a housing cover attached in a leak-resistant manner to said center housing member; and
 a retractable blade assembly attached to said center housing member and said bottom housing member wherein said blade assembly is retractable into said housing when the unit is not in use, said housing cover further comprising its top surface being at a sloped angle when said housing cover is attached to said center housing member, the abutting edges of said cover and said housing member being stepped with an outer downwardly extending portion on said cover mating in a fluid tight manner with a groove on said center housing member.

14. In the unit of claim 13 wherein said housing cover further comprises its top surface being at a sloped angle when said housing cover is attached to said center housing member.

15. In the unit of claim 13 wherein said blade assembly further comprises a plurality of O-rings associated therewith to prevent travel or accumulation of water across the blades.

16. A compact contact lens disinfection unit comprising:
 a case for containing the contact lenses;
 a bottom housing member;
 a center housing member attached to said bottom housing member in a leak-resistant manner;
 a cap for closing off said center housing member attached to said center housing member; and
 a clip attached to both said center housing member and said cap, said clip and said center housing member defining a chamber within which said case is received and centered therein.

17. In the unit of claim 16 further comprising a retractable blade assembly attached to said bottom housing member and said center housing member, said blade assembly being retractable back into said unit when the unit is not in use.

18. In the unit of claim 16 wherein said case is a dual compartment lens case removably mounted in said chamber.

19. In the unit of claim 16 further comprising a pair of detachable covers covering each of said compartments in said case, each of said covers being biased into a closed position on its respective compartment when said case is disposed in said chamber thereby preventing removal thereof until said case is removed from said chamber.

20. A compact heat disinfection unit for sterilizing contact lenses comprising:
 a housing having an internal chamber adapted to receive a covered dual compartment lens case therein;
 heating means disposed in said unit adjacent to said cavity for heating the same;
 a retractable electric blade assembly coupled to said heating means for providing electricity to the same when said blade assembly is plugged into an electric socket; and
 a button accessible from the exterior of the unit for actuating said heating means, said housing including a first bottom housing member, said button and said heating means being mounted therein, a second center housing member providing a bottom wall of said chamber and a portion of upstanding side walls forming said chamber mounted on top of said housing, said first and second housing members having said blade assembly mounted therein, and a cap closing off the upper end of said second housing member.

21. In the unit of claim 20 wherein the abutting edges of said first and second housing members and said cap are stepped with an outer downwardly extending portion mating with a slot in the mating portion to provide a leak proof unit.

22. In the unit of claim 20 including a resilient clip mounted in said housing between said cap and said second housing member, said clip mating with the side walls forming said chamber, thereby providing a cover for said chamber, said clip being biased in a direction toward the interior of said chamber.

* * * * *